US00PP37428P2

(12) United States Plant Patent
Chen

(10) Patent No.: US PP37,428 P2
(45) Date of Patent: May 19, 2026

(54) ***SPATHIPHYLLUM* PLANT NAMED 'SP2568'**

(50) Latin Name: *Spathiphyllum kochii*
Varietal Denomination: SP2568

(71) Applicant: Flores Laeti, Den Hoorn (NL)

(72) Inventor: Chao-Lun Chen, Taiwan (TW)

(73) Assignee: Flores Laeti (NL)

( * ) Notice: Subject to any disclaimer, the term of this patent is extended or adjusted under 35 U.S.C. 154(b) by 0 days.

(21) Appl. No.: 19/303,053

(22) Filed: Aug. 18, 2025

(51) Int. Cl.
*A01H 5/12* (2018.01)
*A01H 6/10* (2018.01)

(52) U.S. Cl.
USPC ..... Plt./364

(58) Field of Classification Search
USPC ..... Plt./364
See application file for complete search history.

*Primary Examiner* — Susan Mccormick Ewoldt
*Assistant Examiner* — Zachariah Allan Kay

(57) ABSTRACT

A new and distinct cultivar of *Spathiphyllum* plant named 'SP2568' is disclosed, characterized by dark green foliage with distinct, large, blocky cream colored variegated blotches. Foliage is fully formed. Plants produce abundant side shoots, forming a bushy plant. Spathes are pure white, occasionally with unique green variegation. Plants are compact with a moderate growth rate. The new cultivar is a *Spathiphyllum*, normally used for indoor ornamental purposes.

3 Drawing Sheets

Latin name of the genus and species: *Spathiphyllum kochii*.

Cultivar denomination: 'SP2568'.

BACKGROUND OF THE INVENTION

The new *Spathiphyllum* cultivar is the result of a naturally occurring whole plant mutation of an unnamed, unpatented *Spathiphyllum kochii*. No stimulus or product was applied to the parent plant to induce the natural mutation resulting in the claimed plant. *Spathiphyllum* 'SP2568' was found and selected by the inventor in a nursery in Puli Township, Nantou County, Taiwan in September of 2018.

Asexual reproduction of the new cultivar has been performed by both vegetative cuttings and tissue culture. Asexual reproduction was first performed at the same nursery in Puli Township, Nantou County, Taiwan in September of 2019. This propagation and subsequent tissue culture propagation, have shown that the unique features of this cultivar are stable and reproduced true to type in multiple successive generations.

SUMMARY OF THE INVENTION

The cultivar 'SP2568' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SP2568' These characteristics in combination distinguish 'SP2568' as a new and distinct *Spathiphyllum* cultivar:

1. Dark green foliage with distinct, large, blocky cream colored variegated blotches.
2. Fully formed leaves, uniquely combined with variegation on the foliage. Some *Spathiphyllum* varieties known to the inventor with variegated foliage have incomplete or malformed foliage.
3. Pure white spathe, or about 40% of spathes are pure white with green variegation.
4. Abundant side shoot production, forming a bushy plant.
5. Compact plant habit with a moderate growth rate. From a tissue culture plant to a finished product in a 5 to 6 inch pot takes about 12 months.

PARENT COMPARISON

Plants of the new cultivar *Spathiphyllum* 'SP2568' are similar to plants of the parent in most horticultural characteristics; however, plants of the new cultivar 'SP2568' differ in the following:

1. Foliage color of the new cultivar is dark green with distinct, large, blocky cream colored variegated blotches. Foliage color of the parent variety is solid green.
2. The new cultivar has a two-color spathe; the parent variety has a solid white spathe.
3. Plants of the new cultivar are not as vigorous as plants of the parent variety. The new cultivar takes approximately 25% more time to grow into a plant of the same size as the parent.

COMMERCIAL COMPARISONS

Plants of the new cultivar 'SP2568' are comparable to the commercial variety *Spathiphyllum* 'City of Angels', unpatented. The two *Spathiphyllum* varieties are similar in most horticultural characteristics, however, the new cultivar 'SP2568' differs in the following:

1. 'City of Angels' has longer and narrower leaves than the new cultivar.
2. 'City of Angels' has incomplete leaf formation along variegated (cream) parts.

3. 'City of Angels' has speckling through its variegation; the new cultivar has a blocky variegation pattern.
4. 'City of Angels' has a longer and wider spathe.
5. 'City of Angels' has a white spathe color; the new cultivar has a green and white spathe.

Plants of the new cultivar 'SP2568' are comparable to the commercial variety *Spathiphyllum* 'Domino', U.S. Plant Pat. No. 9,944. The two *Spathiphyllum* varieties are similar in most horticultural characteristics, however, the new cultivar 'SP2568' differs in the following:

1. 'Domino' has a pure white spathe color; the new cultivar has a green and white spathe.
2. Spathes of 'Domino' are approximately half the size of spathes of the new cultivar.

BRIEF DESCRIPTION OF THE PHOTOGRAPHS

The accompanying photographs illustrate in full color a typical plant of the new cultivar, 'SP2568' grown in a greenhouse in Nantou County, Taiwan. The photographs were taken using conventional techniques and although colors may appear different from actual colors due to light reflectance it is as accurate as possible by conventional photographic techniques.

DETAILED BOTANICAL DESCRIPTION

Figure 1:
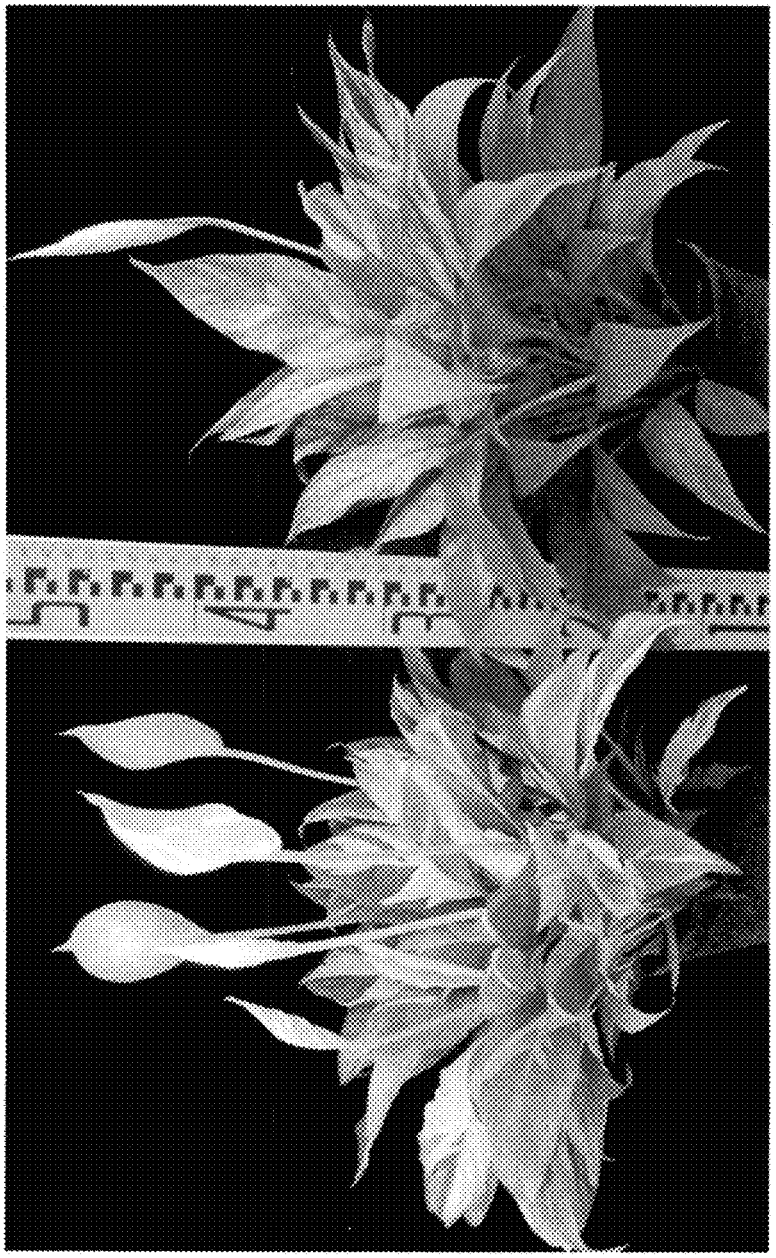
FIG. 1 illustrates a flowering plant 'SP2568' on the left of the photo and a plant of the comparator 'City of Angels' on the right of the photo. These plants are approximately 9 months old.
Figure 2:
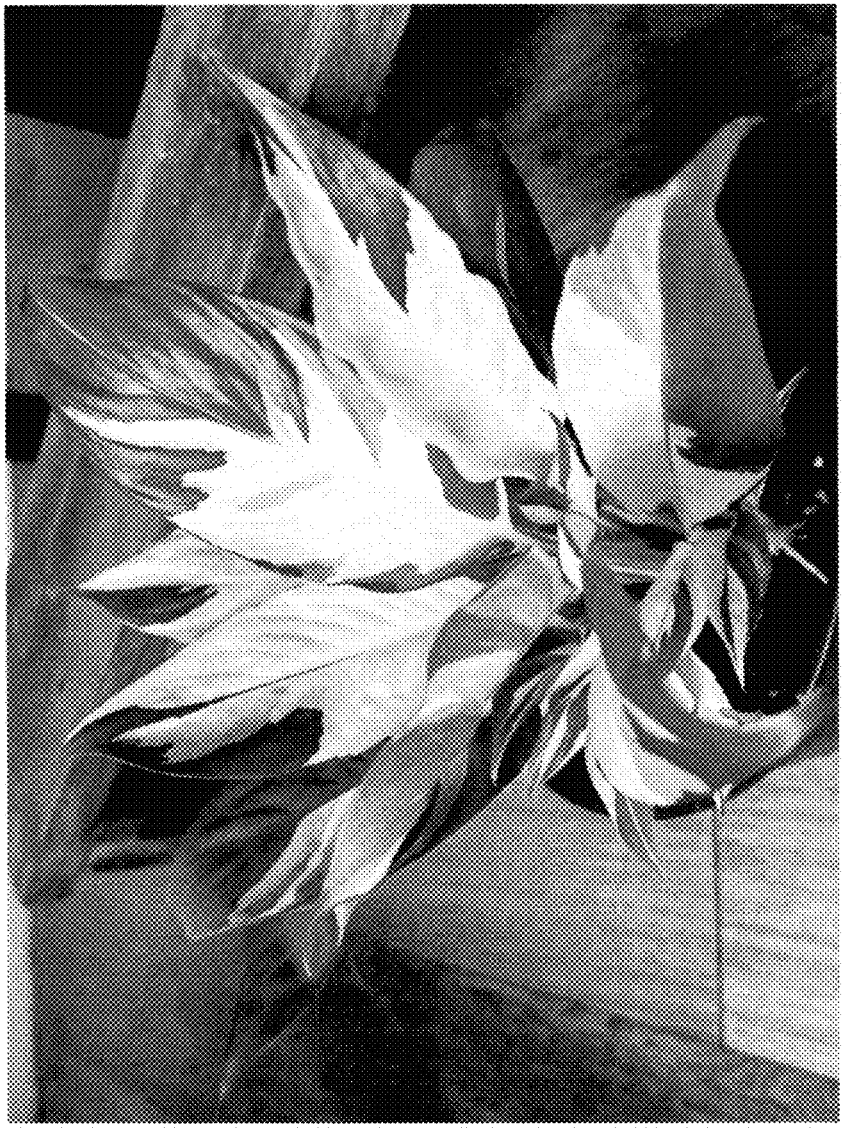
FIG. 2 illustrates a non-flowering plant of 'SP2568' at approximately 5 months of age.
Figure 3:
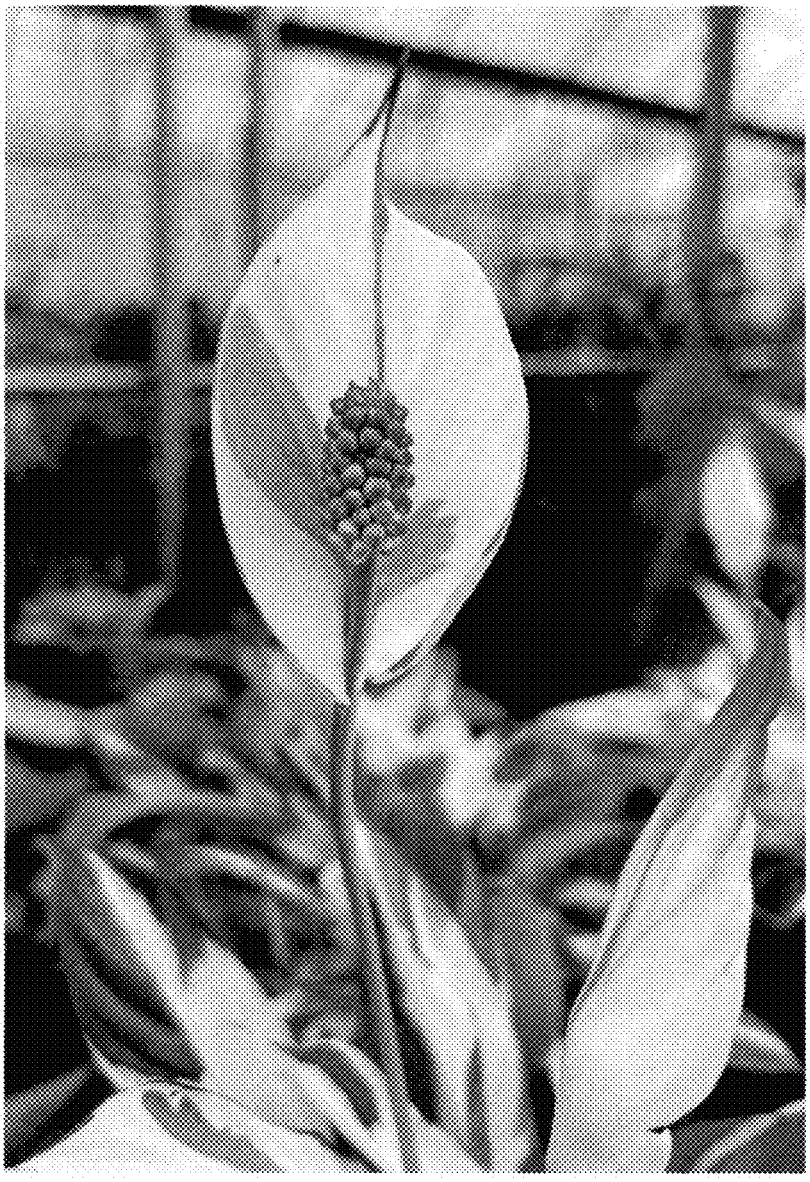
FIG. 3 illustrates a white and green variegated spathe of 'SP2568'

In the following description, color references are made to The Royal Horticultural Society Colour Chart 6$^{th}$ Edition 2015 except where general terms of ordinary dictionary significance are used. The following observations and measurements describe 'SP2568' plants grown in a greenhouse in Vista, CA. The growing temperature ranged from approximately 20° C. to 25° C. during the day and from approximately 18° C. to 20° C. during the night. General light conditions are normal sunlight and numerical values represent averages of typical plant types.

Botanical classification: *Spathiphyllum kochii* 'SP2568'.

PROPAGATION

Time to initiate roots: Approximately 18 days at approximately 25° C. soil temperature.

Time to produce a fully rooted plantlet: Approximately 14 weeks at approximately 20° C. to 30° C. soil temperature.

Root description: Thick, fleshy roots with fine, fibrous lateral roots. Color near Orange-White 158D.

PLANT

Age of plant described: 50 weeks old from a rooted cutting.

Container size: 6-inch pot.

Plant shape: Inverted triangle.

Height: Approximately 35 cm to top of foliar plane. Approximately 45 to 48 cm to top of tallest spathe.

Plant spread: Approximately 55 to 60 cm in a 6 inch pot.

Pot size of plant described: 6 inch.

Growth rate: Moderate. From a tissue culture plant to a finished product in a 5 to 6 inch pot takes about 12 months.

Branching characteristics: No true branching. Leaves emerge directly from base of plant.

Number of clumps of leaves: 10.

Number of leaves per clump: Average 4 to 8.

Number of leaves per plant: Approximately 50 to 70.

Age of plant described: Approximately 20 weeks.

FOLIAGE

Leaf:

*Arrangement*.—Basally emerging.

*Average length* (*excluding petiole*).—11 to 14 cm.

*Average width*.—Approximately 4 cm.

*Shape of blade*.—Elliptic.

*Aspect*.—Undulate.

*Apex*.—Weakly cirrose.

*Base*.—Attenuate.

*Margin*.—Entire.

*Texture of top surface*.—Glabrous.

*Texture of bottom surface*.—Glabrous.

*Color*.—Young foliage upper side: White 155A. irregular blotching with Green 139A and NN137A. Within the green blotching infrequent smaller blotches of NN137C. Very thin marginal coloration Green 139A. Young foliage under side: White 155A. irregular blotching with Green NN137A. Very thin marginal coloration Green 139A. Mature foliage upper side: Color blocked Green 139A, NN137A and White 155A. Within the green blotching infrequent smaller blotches of NN137C. Very thin marginal coloration Green 139A. Mature foliage under side: Color blocked Green NN137A and White 155A. Within the green blotching infrequent smaller blotches of NN137C. Very thin marginal coloration Green 139A.

Venation:

*Type*.—Pinnate.

*Venation coloration upper side*.—Indistinguishable from leaf blade. Following the color pattern of the leaf blade. Green 139A, NN137A and White 155A. Within the green blotching infrequent smaller blotches of NN137C. Venation coloration under side: Indistinguishable from leaf blade. Following the color pattern of the leaf blade. Green NN137A and White 155A. Within the green blotching infrequent smaller blotches of NN137C.

Petiole (excluding wing):

*Length*.—Approximately 7 cm.

*Width*.—At geniculum: 4 to 5 mm. Above clump: Approximately 7 mm.

*Color*.—Green-White 157D.

*Texture*.—Glabrous.

Geniculum:

*Length*.—Approximately 1.5 cm.

*Width*.—Approximately 6 mm.

*Color*.—Green-White 157D.

Wing:

*Length*.—Approximately 4 cm.

*Width*.—At geniculum: 4 to 6 mm. Above clump: Approximately 5 mm.

*Color*.—Green-White 157D. With age a very thin Green margin develops; Green 139B.

*Texture*.—Glabrous.

FLOWER

Arrangement: Spathes with spadices held above the foliage on erect peduncles arising from the petiole sheath.

Flowering habit: Continuous.

Quantity of spathes per plant: On average 4 or 5 fully open spathes in good condition.

Fragrance: None.

Self-cleaning or persistent: Persistent.

Flower longevity: Flowers stay in good condition (no browning or desiccation) approximately 5 weeks on the plant.

Spathe:

*Aspect*.—Cupped.

*Length*.—Approximately 10 cm.

*Width*.—Approximately 8 cm.

*Shape*.—Ovate.

*Margin*.—Entire.

*Apex*.—Short cirrose.

*Base*.—Cuneate, non-symmetrical.

*Color*.—Front when opening: Near RHS White NN155C. About 40% of spathes have green blotching. Blotching colored Green 143A streaked 143C. Apex 141D. Mid vein 143A. Back when opening: Near RHS White NN155C. About 40% of spathes have green blotching. Blotching colored Green 143A streaked 143C. Apex 141D. Mid vein 143A. Front when mature: Near RHS White NN155C. About 40% of spathes have green blotching. Blotching colored Green 143A streaked 143C. Apex 141D. Mid vein 143A. Back when mature: Near RHS White NN155C. About 40% of spathes have green blotching. Blotching colored Green 143A streaked 143C. Apex 141D. Mid vein 143A.

Spadix:

*Shape*.—Columnar, arising from the top of the peduncle.

*Tip*.—Obtuse.

*Base*.—Obtuse.

*Length*.—Approximately 3.5 cm.

*Width*.—Approximately 2.5 cm.

*Color*.—RHS Orange-White 159D.

*Quantity of flowers per spadix*.—Approximately 70.

*Spadix flower arrangement*.—Bisexual, rounded.

*Spadix flower diameter*.—Approximately 3 mm.

*Spadix flower depth*.—Approximately 3 mm.

Peduncle:

*Length*.—Approximately 20 to 25 cm, measured from base, which emerges from leaf axil.

*Width*.—Approximately 6 mm.

*Color*.—Near RHS Green 143B.

*Strength*.—Very strong, resisting breakage or lodging.

REPRODUCTIVE ORGANS

Not observed to date.

OTHER CHARACTERISTICS

Fruits and seeds: Not observed to date.

Disease/pest resistance: Neither resistance nor susceptibility to other normal diseases and pests of *Spathiphyllum* observed.

Temperature range: About 5° C. to 40° C.

What is claimed is:

1. A new and distinct cultivar of *Spathiphyllum* plant named 'SP2568' as herein illustrated and described.

* * * * *